United States Patent [19]

Ayer

[11] 4,202,970
[45] May 13, 1980

[54] 11-DEOXY-TRANS-4,5-DIDEHYDRO-PGI₁ COMPOUNDS

[75] Inventor: Donald E. Ayer, Kalamazoo, Mich.

[73] Assignee: The Upjohn Company, Kalamazoo, Mich.

[21] Appl. No.: 938,549

[22] Filed: Aug. 31, 1978

Related U.S. Application Data

[63] Continuation-in-part of Ser. No. 821,542, Aug. 3, 1977.

[51] Int. Cl.² ............................................ C07D 307/93
[52] U.S. Cl. ................................... 542/426; 542/429; 260/346.22; 260/346.73
[58] Field of Search ...................... 260/346.22, 346.73; 542/418, 421, 426, 429

[56] References Cited

PUBLICATIONS

Corey et al., J.A.C.S. 99:4/Mar. 1977, pp. 2006–2008.

*Primary Examiner*—Henry R. Jiles
*Assistant Examiner*—Bernard Dentz
*Attorney, Agent, or Firm*—Robert A. Armitage

[57] ABSTRACT

The present invention relates to certain structural and pharmacological analogs of prostacyclin (PGI₂) which are 11-deoxy-trans-4,5-didehydro-PGI₁ compounds. These novel pharmacological agents are useful as smooth muscle stimulators.

63 Claims, No Drawings

11-DEOXY-TRANS-4,5-DIDEHYDRO-PGI$_1$ COMPOUNDS

CROSS REFERENCE TO RELATED APPLICATION

The present application is a continuation-in-part of Ser. No. 821,542, filed Aug. 3, 1977, now pending.

The present invention provides novel pharmacological agents, the preparation and use of which is described in U.S. Pat. No. 4,109,182, issued Aug. 22, 1978, the relevant portion of which is incorporated here by reference. These pharmacological agents are characterized by smooth muscle stimulatory actions and are related structurally to prostacyclin, being 11-deoxy-trans-4,5-didehydro-PGI$_1$ compounds.

I claim:
1. A prostacyclin analog of the formula

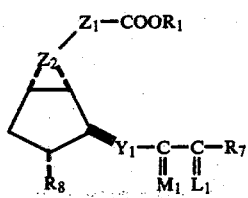

wherein Y$_1$ is trans—CH=CH—, cis—CH=CH—, or —CH$_2$CH$_2$—;
wherein Z$_2$ is

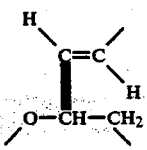

or

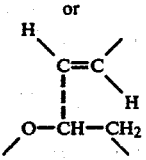

wherein Z$_1$ is
(1) —(CH$_2$)$_g$—CH$_2$—CH$_2$—, or
(2) —(CH$_2$)$_g$—CH$_2$—CF$_2$—,
wherein g is the integer zero, one, or 2;
wherein R$_8$ is hydrogen or hydroxymethyl;
wherein M$_1$ is

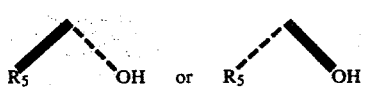

wherein R$_5$ is hydrogen or alkyl with one to 4 carbon atoms, inclusive,
wherein L$_1$ is

or a mixture of

and

wherein R$_3$ and R$_4$ are hydrogen, methyl, or fluoro, being the same or different, with the proviso that one of R$_3$ and R$_4$ is fluoro only when the other is hydrogen or fluoro;
wherein R$_1$ is hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, two or three chloro or alkyl of one to 3 carbon atoms; phenyl substituted in the para position by

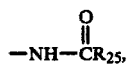 (a)

 (b)

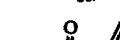 (c)

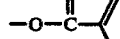 (d)

wherein R$_{25}$ is methyl, phenyl, acetamidophenyl, benzamidophenyl, or —NH$_2$; R$_{26}$ is methyl, phenyl, —NH$_2$, or methoxy; and R$_{27}$ is hydrogen or acetamido, inclusive; phenacyl, i.e.,

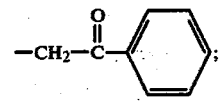

phenacyl substituted in the para position by chloro, bromo, phenyl, or benzamido; or a pharmacologically acceptable cation;
wherein R$_7$ is

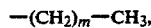 (1)

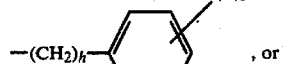 (2)

 (3)

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl.

2. A prostacyclin analog according to claim 1, wherein $Y_1$ is trans—CH=CH—.

3. A prostacyclin analog according to claim 2, wherein $R_8$ is hydroxymethyl.

4. A prostacyclin analog according to claim 3, wherein $Z_2$ is a mixture of

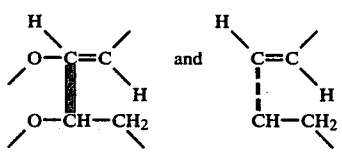

5. trans-4,5-Didehydro-(6RS)-deoxy-11α-hydroxymethyl-PGI$_1$, a prostacyclin analog according to claim 4.

6. A prostacyclin analog according to claim 3, wherein $Z_2$ is

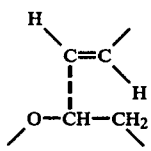

7. trans-4,5-Didehydro-6α-11-deoxy-11α-hydroxymethyl-PGI$_1$, a prostacyclin analog according to claim 6.

8. 15-Methyl-trans-4,5-didehydro-6α-11-deoxy-11α-hydroxymethyl-PGI$_1$, a prostacyclin analog according to claim 6.

9. 16,16-Dimethyl-trans-4,5-didehydro-6α-11-deoxy-11α-hydroxymethyl-PGI$_1$, a prostacyclin analog according to claim 6.

10. 16,16-Difluoro-trans-4,5-didehydro-6α-11-deoxy-11α-hydroxymethyl-PGI$_1$, a prostacyclin analog according to claim 6.

11. A prostacyclin analog according to claim 3, wherein $Z_2$ is

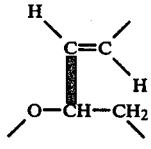

12. A prostacyclin analog according to claim 11, wherein $Z_1$ is —(CH$_2$)$_g$—CH$_2$—CF$_2$—.

13. 2,2-Difluoro-trans-4,5-didehydro-6β-11-deoxy-11α-hydroxymethyl-PGI$_1$, a prostacyclin analog according to claim 12.

14. A prostacyclin analog according to claim 11, wherein $Z_1$ is —(CH$_2$)$_g$—CH$_2$—CH$_2$—.

15. A prostacyclin analog according to claim 14, wherein g is zero.

16. A prostacyclin analog according to claim 15, wherein $R_7$ is

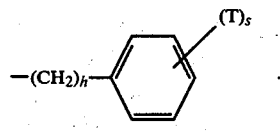

17. 17-Phenyl-18,19,20-trinor-trans-4,5-didehydro-6β-11-deoxy-11α-hydroxymethyl-PGI$_1$, a prostacyclin analog according to claim 16.

18. A prostacyclin analog according to claim 15, wherein $R_7$ is

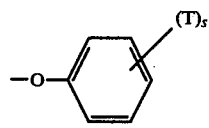

19. 16-Phenoxy-17,18,19,20-tetranor-trans-4,5-didehydro-6β-11-deoxy-11α-hydroxymethyl-PGI$_1$, a prostacyclin analog according to claim 18.

20. A prostacyclin analog according to claim 15, wherein $R_7$ is —(CH$_2$)$_m$—CH$_3$—.

21. A prostacyclin analog according to claim 20, wherein m is 3.

22. A prostacyclin analog according to claim 21, wherein $R_5$ is methyl.

23. 15-Methyl-trans-4,5-didehydro-6β-11-deoxy-11α-hydroxymethyl-PGI$_1$, a prostacyclin analog according to claim 22.

24. A prostacyclin analog according to claim 21, wherein $R_5$ is hydrogen.

25. A prostacyclin analog according to claim 24, wherein at least one of $R_3$ and $R_4$ is fluoro.

26. 16,16-Difluoro-trans-4,5-didehydro-6β-11-deoxy-11α-hydroxymethyl-PGI$_1$, a prostacyclin analog according to claim 25.

27. A prostacyclin analog according to claim 24, wherein at least one of $R_3$ and $R_4$ is methyl.

28. 16,16-Dimethyl-trans-4,5-didehydro-6β-11-deoxy-11α-hydroxymethyl-PGI$_1$, a prostacyclin analog according to claim 27.

29. A prostacyclin analog according to claim 24, wherein $R_3$ and $R_4$ are both hydrogen.

30. trans-4,5-Didehydro-6β-11-deoxy-11α-hydroxymethyl-PGI$_1$, methyl ester, a prostacyclin analog according to claim 29.

31. trans-4,5-Didehydro-6β-11-deoxy-11α-hydroxymethyl-PGI$_1$, tris(hydroxymethyl)amino methane salt, a prostacylin analog according to claim 29.

32. trans-4,5-Didehydro-6β-11-deoxy-11α-hydroxymethyl-PGI$_1$, adamantanamine salt, a prostacyclin analog according to claim 29.

33. trans-4,5-Didehydro-6β-11-deoxy-11α-hydroxymethyl-PGI$_1$, a prostacyclin analog according to claim 29.

34. A prostacyclin analog according to claim 2, wherein $R_8$ is hydrogen.

35. A prostacyclin analog according to claim 34, wherein $Z_2$ is a mixture of

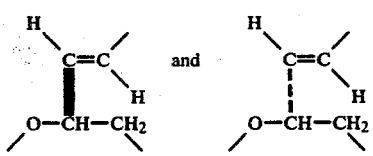 and 36. trans-4,5-Didehydro-(6RS)-11-deoxy-PGI₁, a prostacyclin analog according to claim 35.

37. A prostacyclin analog according to claim 34, wherein Z₂ is

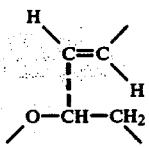

38. trans-4,5-Didehydro-6α-11-deoxy-PGI₁, a prostacyclin analog according to claim 37.

39. 15-Methyl-trans-4,5-didehydro-6α-11-deoxy-PGI₁, a prostacyclin analog according to claim 37.

40. 16,16-Dimethyl-trans-4,5-didehydro-6α-11-deoxy-PGI₁, a prostacyclin analog according to claim 37.

41. A prostacyclin analog according to claim 34, wherein Z₂ is

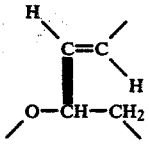

42. A prostacyclin analog according to claim 41, wherein Z₁ is —(CH₂)$_g$—CH₂—CF₂—.

43. 2,2-Difluoro-trans-4,5-didehydro-6β-11-deoxy-PGI₁, a prostacyclin analog according to claim 42.

44. A prostacyclin analog according to claim 41, wherein Z₁ is —(CH₂)$_g$—CH₂—CH₂—.

45. A prostacyclin analog according to claim 44, wherein g is zero.

46. A prostacyclin analog according to claim 45, wherein R₇ is

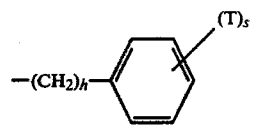

47. 17-Phenyl-18,19,20-trinor-trans-4,5-didehydro-6β-11-deoxy-PGI₁, a prostacyclin analog according to claim 46.

48. A prostacyclin analog according to claim 45, wherein R₇ is

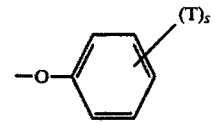

49. 16-Phenoxy-17,18,19,20-tetranor-trans-4,5-didehydro-6β-11-deoxy-PGI₁, a prostacyclin analog according to claim 48.

50. A prostacyclin analog according to claim 45, wherein R₇ is —(CH₂)$_m$—CH₃.

51. A prostacyclin analog according to claim 50, wherein m is 3.

52. A prostacyclin analog according to claim 51, wherein R₅ is methyl.

53. 15-Methyl-trans-4,5-didehydro-6β-11-deoxy-PGI₁, a prostacyclin analog according to claim 52.

54. A prostacyclin analog according to claim 51, wherein R₅ is hydrogen.

55. A prostacyclin analog according to claim 54, wherein at least one of R₃ and R₄ is fluoro.

56. 16,16-Difluoro-trans-4,5-didehydro-6β-11-deoxy-PGI₁, a prostacyclin analog according to claim 55.

57. A prostacyclin analog according to claim 54, wherein at least one of R₃ and R₄ is methyl.

58. 16,16-Dimethyl-trans-4,5-didehydro-6β-11-deoxy-PGI₁, a prostacyclin analog according to claim 57.

59. A prostacyclin analog according to claim 54, wherein R₃ and R₄ are both hydrogen.

60. trans-4,5-Didehydro-6β-11-deoxy-PGI₁, methyl ester, a prostacyclin analog according to claim 59.

61. trans-4,5-Didehydro-6β-11-deoxy-PGI₁, tris(hydroxymethyl)amino methane salt, a prostacyclin analog according to claim 59.

62. trans-4,5-Didehydro-6β-11-deoxy-PGI₁, adamantanamine salt, a prostacyclin analog according to claim 59.

63. trans-4,5-Didehydro-6β-11-deoxy-PGI₁, a prostacyclin analog according to claim 59.

* * * * *